United States Patent
Ono et al.

(10) Patent No.: US 6,775,817 B2
(45) Date of Patent: Aug. 10, 2004

(54) INSPECTION SYSTEM AND SEMICONDUCTOR DEVICE MANUFACTURING METHOD

(75) Inventors: Makoto Ono, Tokyo (JP); Hisafumi Iwata, Tokyo (JP); Keiko Kirino, Tokyo (JP)

(73) Assignee: Hitachi, Ltd. (JP)

( * ) Notice: Subject to any disclaimer, the term of this patent is extended or adjusted under 35 U.S.C. 154(b) by 0 days.

(21) Appl. No.: 10/004,168

(22) Filed: Oct. 30, 2001

(65) Prior Publication Data

US 2002/0052053 A1 May 2, 2002

(30) Foreign Application Priority Data

Oct. 30, 2000 (JP) ........................................ 2000-334915

(51) Int. Cl.⁷ .............................................. G06F 17/50
(52) U.S. Cl. ......................................... 716/21; 702/84
(58) Field of Search ............................... 716/19–21, 2, 716/4; 702/84

(56) References Cited

U.S. PATENT DOCUMENTS

| | | | | |
|---|---|---|---|---|
| 4,618,938 A | * | 10/1986 | Sandland et al. ............ | 382/148 |
| 5,539,514 A | * | 7/1996 | Shishido et al. .......... | 356/237.4 |
| 5,598,341 A | * | 1/1997 | Ling et al. .................... | 700/110 |
| 5,777,901 A | * | 7/1998 | Berezin et al. ................ | 716/19 |
| 6,047,083 A | * | 4/2000 | Mizuno ....................... | 382/141 |
| 6,128,403 A | * | 10/2000 | Ozaki ......................... | 382/145 |
| 6,169,960 B1 | * | 1/2001 | Ehrichs ........................ | 702/36 |
| 6,272,236 B1 | * | 8/2001 | Pierrat et al. ................ | 382/144 |
| 6,324,481 B1 | * | 11/2001 | Atchison et al. .............. | 702/84 |
| 6,334,209 B1 | * | 12/2001 | Hashimoto et al. ........... | 716/21 |
| 6,393,602 B1 | * | 5/2002 | Atchison et al. ................ | 716/4 |
| 6,401,235 B1 | * | 6/2002 | Ashida ......................... | 716/19 |
| 6,411,377 B1 | * | 6/2002 | Noguchi et al. .......... | 356/237.4 |
| 6,438,438 B1 | * | 8/2002 | Takagi et al. ................ | 700/121 |
| 6,507,933 B1 | * | 1/2003 | Kirsch et al. .................. | 716/4 |
| 6,539,272 B1 | * | 3/2003 | Ono et al. ................... | 700/110 |
| 2001/0020194 A1 | * | 9/2001 | Takagi et al. ................ | 700/109 |

FOREIGN PATENT DOCUMENTS

JP          10-214866          8/1998

* cited by examiner

*Primary Examiner*—Stacy A. Whitmore
(74) *Attorney, Agent, or Firm*—Townsend and Townsend and Crew LLP

(57) ABSTRACT

A method and system are provided for analyzing defects having the potential to become electrical failures, during the inspection of particles and/or pattern defects of a wafer used in the manufacture of electronic devices such as semiconductor integrated circuits. Defect map data is processed along with failure probability data. Next, defect-dependent failure probability calculations are made to obtain the failure probability of each defect in the defect map data. That data is then used to prepare failure-probability-added defect map data. Further, a selection process of defects to be reviewed is used to reorder and filter defects from the failure-probability-added defect map data, thus selecting one or more defects for review.

8 Claims, 12 Drawing Sheets

```
PRODUCT TYPE NAME
    LOGIC234
LAYER NAME
    METAL1                      ─72
BLOCK NAME
    B1
BLOCK COORDINATES
    RECTANGLE DIAGONAL
    ANGLE (5, 80) - (20, 95)
DEFECT          FAILURE
DIAMETER        PROBABILITY
    0.05,           0.00
    0.10,           0.01
    0.15,           0.02
    0.20,           0.03
    0.25,           0.05
     .               .
     .               .
     .               .
    9.95,           1.00
   10.00,           1.00
```

| CHIP NO., | CHIP COLUMN, | CHIP ROW, | X, | Y, | DEFECT DIAMETER |
|---|---|---|---|---|---|
| 1, | 1, | 1, | 73, | 67, | 2.4 |
| 2, | 5, | 1, | 25, | 89, | 0.3 |
| 3, | 4, | 2, | 47, | 69, | 1.5 |
| 4, | 5, | 3, | 80, | 82, | 1.0 |
| 5, | 6, | 5, | 52, | 78, | 1.2 |
| 6, | 3, | 5, | 71, | 32, | 0.2 |
| 7, | 3, | 7, | 87, | 90, | 0.7 |
| 8, | 2, | 6, | 77, | 38, | 0.3 |
| 9, | 0, | 4, | 83, | 45, | 0.8 |
| 10, | 2, | 3, | 49, | 9, | 1.9 |

```
PRODUCT TYPE NAME
   LOGIC234
LAYER NAME
   METAL1
BLOCK NAME
   B1
BLOCK COORDINATES
   RECTANGLE DIAGONAL
   ANGLE (5, 80) - (20, 95)
DEFECT        FAILURE
DIAMETER      PROBABILITY
   0.05,         0.00
   0.10,         0.01
   0.15,         0.02
   0.20,         0.03
   0.25,         0.05
    .             .
    .             .
    .             .
   9.95,         1.00
  10.00,         1.00
```
~72

FIG.11

| NO., | CHIP COL., | CHIP ROW, | X, | Y, | SIZE, | BLOCK, | BLOCK EDGE, | FAILURE PROBABILITY |
|---|---|---|---|---|---|---|---|---|
| 1, | 1, | 1, | 73, | 67, | 2.4, | B5, | no, | 0.83 |
| 2, | 5, | 1, | 25, | 89, | 0.3, | B1, | no, | 0.07 |
| 3, | 4, | 2, | 47, | 69, | 1.5, | B2, | no, | 0.26 |
| 4, | 5, | 3, | 80, | 82, | 1.0, | B5, | no, | 0.38 |
| 5, | 6, | 5, | 52, | 78, | 1.2, | B5, | yes, | 0.50 |
| 6, | 3, | 5, | 71, | 32, | 0.2, | B6, | yes, | 0.05 |
| 7, | 3, | 7, | 87, | 90, | 0.7, | B5, | no, | 0.35 |
| 8, | 2, | 6, | 77, | 38, | 0.3, | B6, | no, | 0.07 |
| 9, | 0, | 4, | 83, | 45, | 0.8, | B5, | no, | 0.28 |
| 10, | 2, | 3, | 49, | 9, | 1.9, | B7, | no, | 0.06 |

FIG.12

| NO., | CHIP COL., | CHIP ROW, | X, | Y, | SIZE, | BLOCK, | BLOCK EDGE, | FAILURE PROBABILITY |
|---|---|---|---|---|---|---|---|---|
| 1, | 1, | 1, | 73, | 67, | 2.4, | B5, | no, | 0.83 |
| 5, | 6, | 5, | 52, | 78, | 1.2, | B5, | yes, | 0.50 |
| 4, | 5, | 3, | 80, | 82, | 1.0, | B5, | no, | 0.38 |
| 7, | 3, | 7, | 87, | 90, | 0.7, | B5, | no, | 0.35 |
| 9, | 0, | 4, | 83, | 45, | 0.8, | B5, | no, | 0.28 |
| 3, | 4, | 2, | 47, | 69, | 1.5, | B2, | no, | 0.26 |
| 8, | 2, | 6, | 77, | 38, | 0.3, | B6, | no, | 0.07 |
| 2, | 5, | 1, | 25, | 89, | 0.3, | B1, | no, | 0.07 |
| 10, | 2, | 3, | 49, | 9, | 1.9, | B7, | no, | 0.06 |
| 6, | 3, | 5, | 71, | 32, | 0.2, | B6, | yes, | 0.05 |

FIG.13

| NO., | CHIP COL., | CHIP ROW, | X, | Y, | SIZE, | BLOCK, | BLOCK EDGE, | FAILURE PROBABILITY |
|---|---|---|---|---|---|---|---|---|
| 1, | 1, | 1, | 73, | 67, | 2.4, | B5, | no, | 0.83 |
| 4, | 5, | 3, | 80, | 82, | 1.0, | B5, | no, | 0.38 |
| 7, | 3, | 7, | 87, | 90, | 0.7, | B5, | no, | 0.35 |
| 9, | 0, | 4, | 83, | 45, | 0.8, | B5, | no, | 0.28 |
| 3, | 4, | 2, | 47, | 69, | 1.5, | B2, | no, | 0.26 |

FIG.14

| NO., | CHIP COL., | CHIP ROW, | X, | Y, | SIZE, | BLOCK, | BLOCK EDGE, | FAILURE PROBABILITY |
|---|---|---|---|---|---|---|---|---|
| 3, | 4, | 2, | 47, | 69, | 1.5, | B2, | no, | 0.26 |
| 8, | 2, | 6, | 77, | 38, | 0.3, | B6, | no, | 0.07 |
| 2, | 5, | 1, | 25, | 89, | 0.3, | B1, | no, | 0.07 |
| 10, | 2, | 3, | 49, | 9, | 1.9, | B7, | no, | 0.06 |
| 6, | 3, | 5, | 71, | 32, | 0.2, | B6, | yes, | 0.05 |

FIG.15

| NO., | CHIP COL., | CHIP ROW, | X, | Y, | SIZE, | BLOCK, | BLOCK EDGE, | FAILURE PROBABILITY |
|---|---|---|---|---|---|---|---|---|
| 1, | 1, | 1, | 73, | 67, | 2.4, | B5, | no, | 0.83 |
| 5, | 6, | 5, | 52, | 78, | 1.2, | B5, | yes, | 0.50 |
| 4, | 5, | 3, | 80, | 82, | 1.0, | B5, | no, | 0.38 |
| 7, | 3, | 7, | 87, | 90, | 0.7, | B5, | no, | 0.35 |
| 9, | 0, | 4, | 83, | 45, | 0.8, | B5, | no, | 0.28 |

PRODUCT TYPE NAME
    LOGIC234
LAYER NAME
    METAL1
MAXIMUM DEFECT NUMBER
    20
OBJECT
    FAILURE PROBABILITY
        0.30 OR GREATER
EXCLUDED
    B5
    BLOCK EDGES B1, B2

41

INSPECTION SYSTEM AND SEMICONDUCTOR DEVICE MANUFACTURING METHOD

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

FIELD OF THE INVENTION

The present invention relates to inspection systems in the manufacture of electronic devices such as semiconductor integrated circuits and also to a methodology for manufacturing electronic devices using this inspection system.

BACKGROUND OF THE INVENTION

In the manufacture of electronic devices typically including semiconductor integrated circuits, after detection of defects using, for example, a dark-field and/or bright-field wafer inspection apparatus, an image taking apparatus with a built-in electron microscope or a similar review apparatus is used in some cases for analyzing the individual defects thus detected. It should be noted that while a dark-field wafer inspection apparatus detects particles attached to wafers, and a bright field wafer inspection apparatus detects pattern defects formed on wafers, such particles and pattern defects will be termed "defects" in the following description.

Currently available review apparatuses are generally designed to sense or pick up the position of an individual defect as an image having higher resolution than is available using dark-field and bright-field wafer inspection apparatuses. Because of this characteristic, such review apparatuses are not for imaging the positions of all possible defects detected by an inspection apparatus but for sampling the defect positions within wafer surfaces and for performing image sensing operations with respect only to several limited surface areas. Traditionally this sampling has been achieved by random sampling—that is, random selection of defects from among those defects detected.

In addition, Published Unexamined Japanese Patent Application No. 10-214866 ("JP-A-10-214866") discloses a technique, in cases where cluster-shaped defects (such as scars) and clustered defects or the like are present, for classifying those defects into defects occurring inside or outside the cluster-like defects. In this case, too, random sampling of several portions from the inside of the cluster-like defects was done while randomly sampling several portions from the outside.

With the prior art random sampling technique, although it is possible to statistically recognize the tendency of defects, the current technologies cannot ensure efficient review of any required defects. For example, it is impossible to provide any priority-added remedy for critical defects that can lead to electrical failures, which, in turn, makes it difficult to effectively improve the resultant yield of production.

SUMMARY OF THE INVENTION

It is therefore a primary aim of the present invention to provide an inspection system capable of improving inspection efficiency by determining certain defects to warrant high-priority review. Another aim is to improve thereby the manufacturing yield of semiconductor devices.

We have taken into careful consideration the relationship of a defect distribution and Large Scale Integration chip (hereinafter "LSI") layout, and propose a specific technique for enabling selection of defects to be given high-priority review.

FIG. 10 is a diagram showing a distribution of defects within the chip to be detected by the inspection apparatus.

This diagram shows the superimposition of dots 35, which represent data about defects detected by the inspection apparatus, onto a schematic diagram 32 of the circuit layout of an LSI chip. More specifically, the detected defects are placed on the LSI schematic diagram using position coordinates within each LSI chip on a wafer. Black dots represent the individual defects. Rectangular frames B1–B7 are the positions of LSI blocks 1–7, respectively. The term "SI block" as used herein refers to an A/D converter block, D/A converter block, memory block, processor block, or the like, in mobile wireless telephone handsets, by way of example. LSI blocks are generally called circuit blocks, which have independent functions within an LSI and their layout is also separate, except for electrical connection of circuits used therein.

As is apparent from the diagram, a distribution of defects detected by the inspection apparatus is closely related to the circuit layout, and exhibits the characteristics which follow.

(1) Defect density is different depending upon the circuit pattern density of the circuit layout. In a region in which the circuit layout is coarse and rough, a greater number of defects will be detected than in dense regions. Generally, the coarse density of circuit pattern differs in units of LSI blocks; for example, processor blocks are narrower in circuit pattern width than memory blocks but have greater layout density. Hence, an increased number of defects are detected in processor blocks than in memory blocks.

(2) At the LSI block edges (contour parts of the circuit layout), a great number of defects are detected. In many cases, this is because the inspection apparatus erroneously identifies as defects objects which are actually not defects. These detection errors occur in areas with greater convex-concave differences in the circuit pattern. Here, the term "edge portion (contour part)" is used to mean a boundary between circuit blocks, which boundary has widths ranging from several tens to several hundreds of micrometers.

Thus, selection through simple random sampling of defects to be reviewed creates another problem: inability to efficiently sample such defects as review candidates, e.g., those defects which have a higher probability of becoming electrical failures.

The present invention resolves the foregoing problems by employing a unique technique using an LSI's design layout to select defects for review. More specifically, LSI design layout information is used to give higher review priority to certain defects that are not in close proximity to LSI block contour portions, or, alternatively, to give higher review priority to defects present in LSI blocks of dense circuit pattern widths.

Moreover, the present invention uses a technique for obtaining failure probability (kill ratio) relative to defect size in the units of LSI blocks and for reviewing high-failure-probability defects. Specified defects most likely to influence production yield are reviewed first, which, in turn, makes it easier and faster to inquire about and clarify several factors having direct influence on production yield in a shorter period of time, thus improving the manufacturing yield. In particular, with a specific type of product having a variety of circuit blocks present in a single LSI, such as the system LSIs, permitting certain defects to be reviewed with higher priority is important for improving yields at earlier stages of the manufacturing process.

BRIEF DESCRIPTION OF THE DRAWINGS

FIG. 11 is an example of failure-possibility-added defect map data.

FIG. 12 is an example of failure-possibility-added defect map data as aligned based on failure possibility.

FIG. 13 is an exemplary selection result for a defect considered for review.

FIG. 14 is another exemplary selection result for a defect considered for review.

FIG. 15 is still another exemplary selection result for a defect considered for review.

FIG. 16 is an example of a review conditions file.

DESCRIPTION OF THE PREFERRED EMBODIMENT

One embodiment of the present invention will now be set forth in detail with reference to the accompanying drawings.

Figures 2, 3:
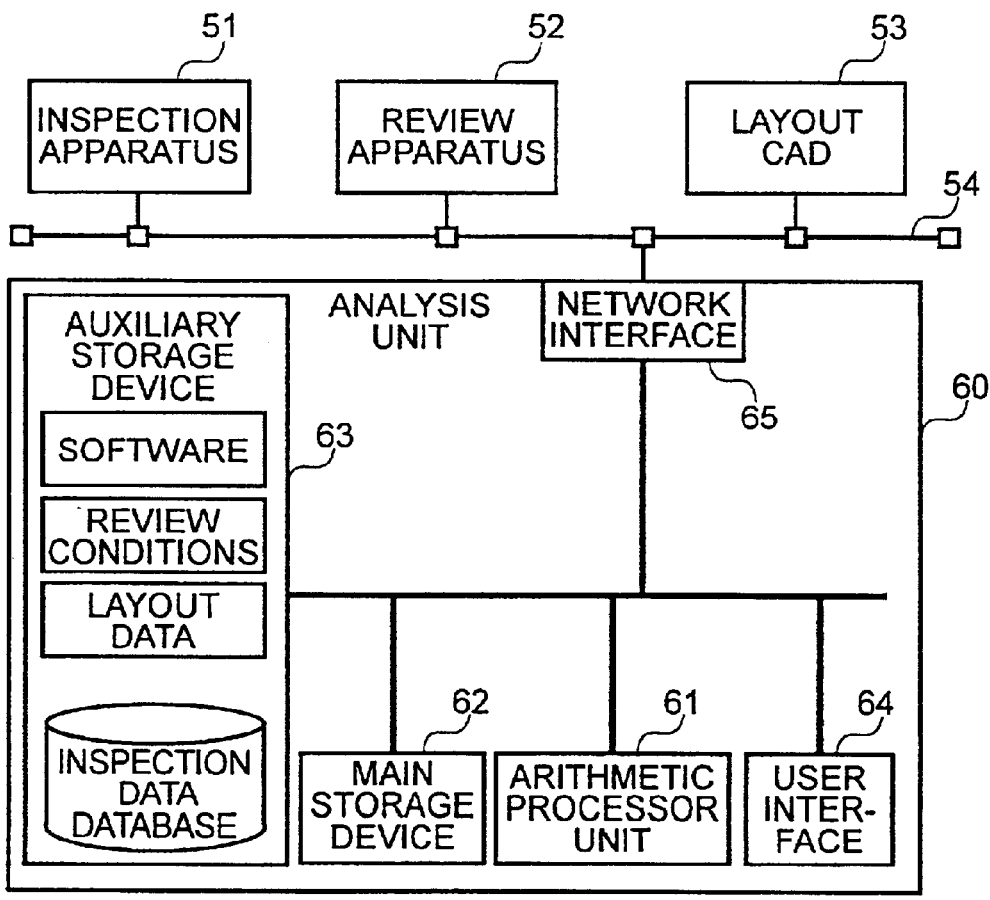
FIG. 2 is a block diagram showing an exemplary arrangement of hardware.
FIG. 3 is an example of defect map data.

FIG. 2 is a block diagram showing one example of a system configuration of the present invention.

The configuration includes an inspection apparatus 51; a review apparatus 52; a layout CAD apparatus 53; and an analysis unit 60, which is a computer system having an arithmetic processor unit 61, a main storage device 62, an auxiliary storage device 63, a user interface 64, and a network interface 65. Inspection apparatus 51, review apparatus 52, layout CAD apparatus 53 and analysis unit 60 are operatively connected and linked via a local area network 54 for data transmission among those components.

Inspection apparatus 51 may be a dark-field wafer inspection apparatus or a bright-field wafer inspection apparatus operable for outputting information about coordinate positions and sizes of defects within wafer surfaces. Defect map data from inspection apparatus 51 is stored in the test database of auxiliary storage device 63 via local area network 54, network interface 65, and main storage device 62 of analysis unit 60, along with data items indicative of product type names, lot numbers, wafer numbers, layer names and so forth.

FIG. 3 shows one example of the defect map data as detected by the inspection apparatus. Defect map data 21 has information concerning the coordinate positions and sizes of defects within wafer surfaces. In the illustrative embodiment, defect map data 21 involves a defect number, chip column, chip row, X- and Y-coordinates and defect diameter as written thereinto on a per-defect basis. The defect number is a through number which is added to a defect detected by the test apparatus. The chip column, chip row and X- and Y-coordinates provide a defect coordinate position. The chip column and chip row indicate the position of a chip within a wafer and the X- and Y-coordinates indicate the position of a defect within a chip. In short, these are descriptions of the states shown in FIGS. 4 and 5.

Figure 4:
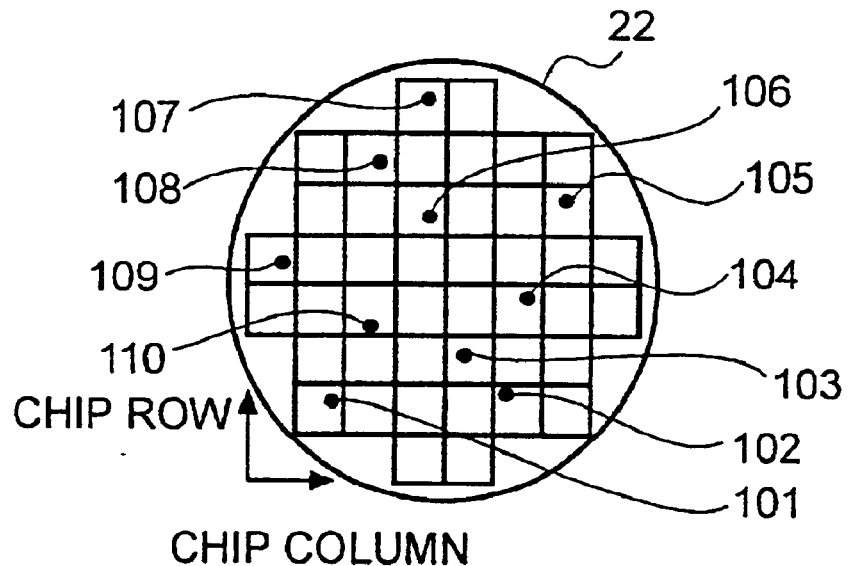
FIG. 4 is an example of the two-dimensional (2D) map data of FIG. 3.

FIG. 4 depicts the defect map data 21 of FIG. 3 as a two-dimensional (2D) map. A circle 22 represents a wafer, rectangular frames inside circle 22 indicate the respective chips. The chip column and chip row of defect map data 21 indicate chip arrays from a wafer edge. Black plotted points 101 to 110 are positions of defects and are analogous to defect numbers 1 to 10 given in defect data map 21, the positions being based on the chip columns and chip rows and the X- and Y-coordinates.

Figure 5:
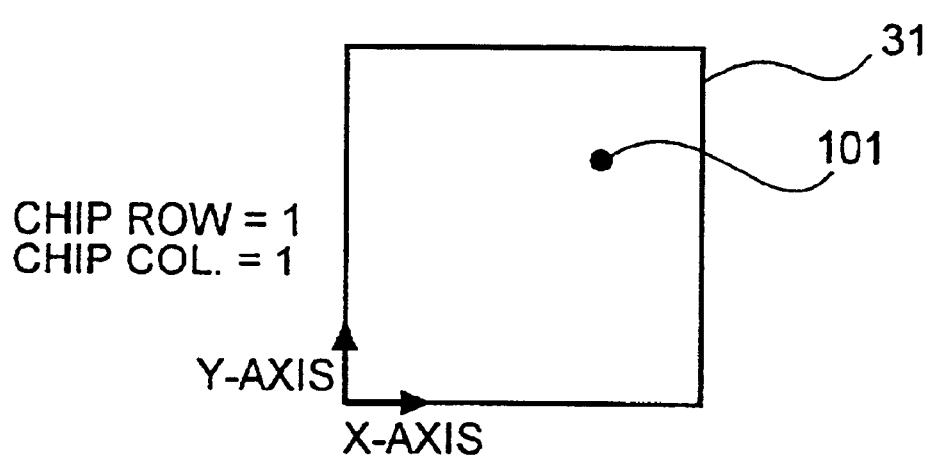
FIG. 5 is an enlarged diagram of a chip row 1 and chip column 1 of FIG. 4.

FIG. 5 shows an enlarged chip belonging to chip column 1 and chip row 1 of FIG. 4. A rectangular frame 31 denotes a chip, wherein the defect 1 of data map 21 is plotted as defect position 101, based on the X- and Y-coordinates from data map 21 which originate, in this figure, at the lower left edge of the chip.

On the other hand, circuit layout data having designs completed by layout CAD apparatus 53 is stored in auxiliary storage device 63, along with a product type name and a layer name, via local area network 54, network interface 65, and main storage device 62 of analysis unit 60. One example is that position information for blocks B1–B7 in a chip (see FIG. 10) is generated from the circuit layout data and stored as layout data in auxiliary storage device 63. Note that this layout data need not be generated exclusively from the layout CAD apparatus and may merely be stored in auxiliary storage device 63 along with the product type name and layer name.

Figures 9, 10:
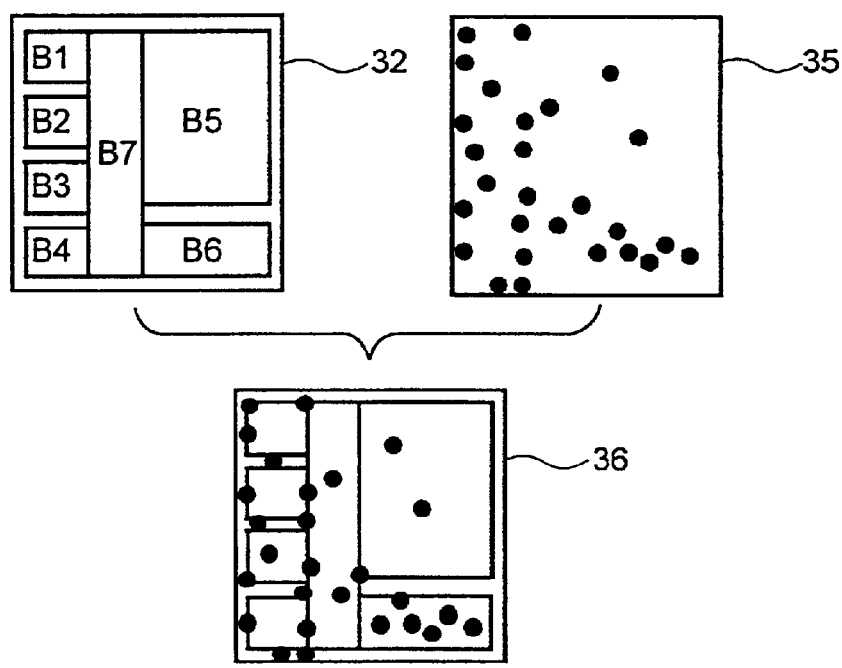
FIG. 9 is an example of a file containing layout data.
FIG. 10 is an example of a relational diagram of defect distribution within a chip versus a circuit layout.

FIG. 9 shows one example of the layout data. With layout data file 72 shown in FIG. 9, the position information of an LSI block b1 is stored together with a product type name LOGIC234, layer name METAL1 and failure probability data for the block name b1, and the coordinates of block b1 refer to a rectangle with the diagonal vertex coordinates X=5, Y=80 and X=20, Y=95 within the chip. In addition, the relation of each defect diameter versus failure probability is described in this file. A layout data file of this type is created for each of the LSI blocks B1–B7 shown in FIG. 10.

Figure 6:
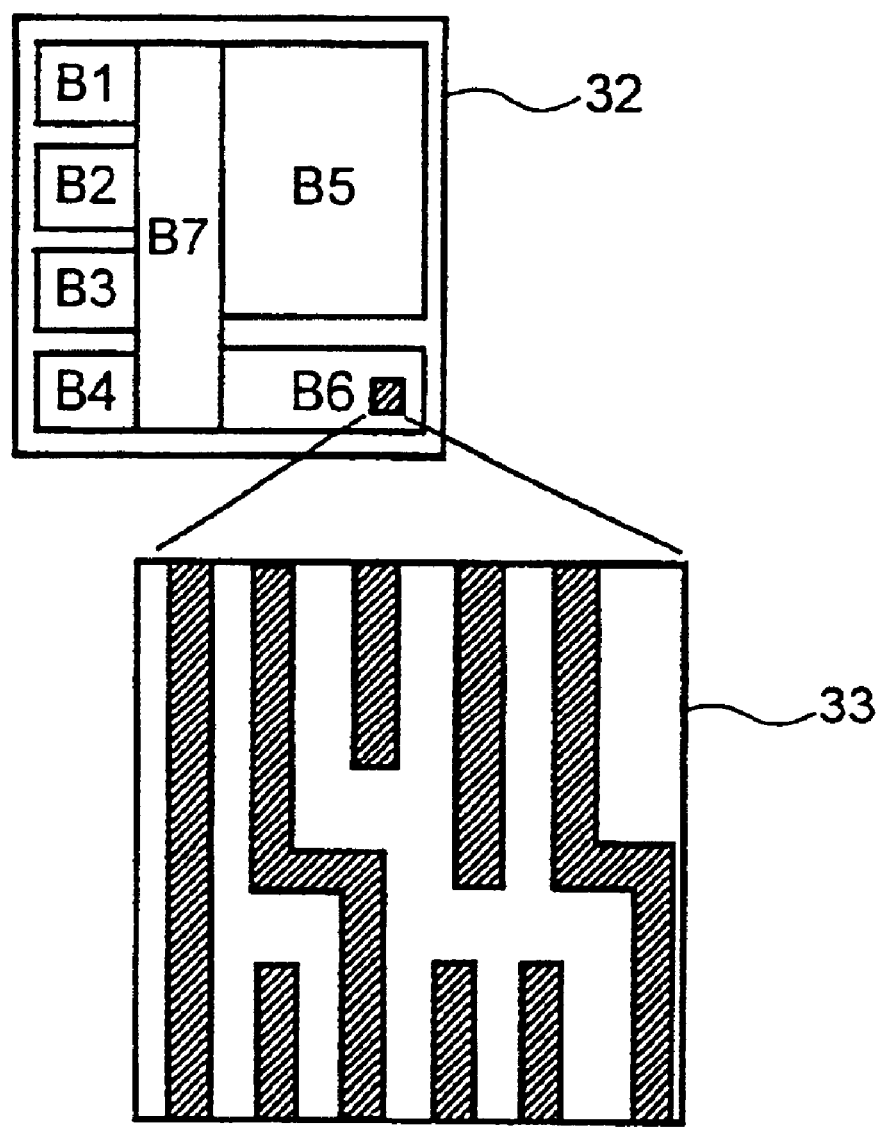
FIG. 6 is an example of circuit layout data.
Figure 7:
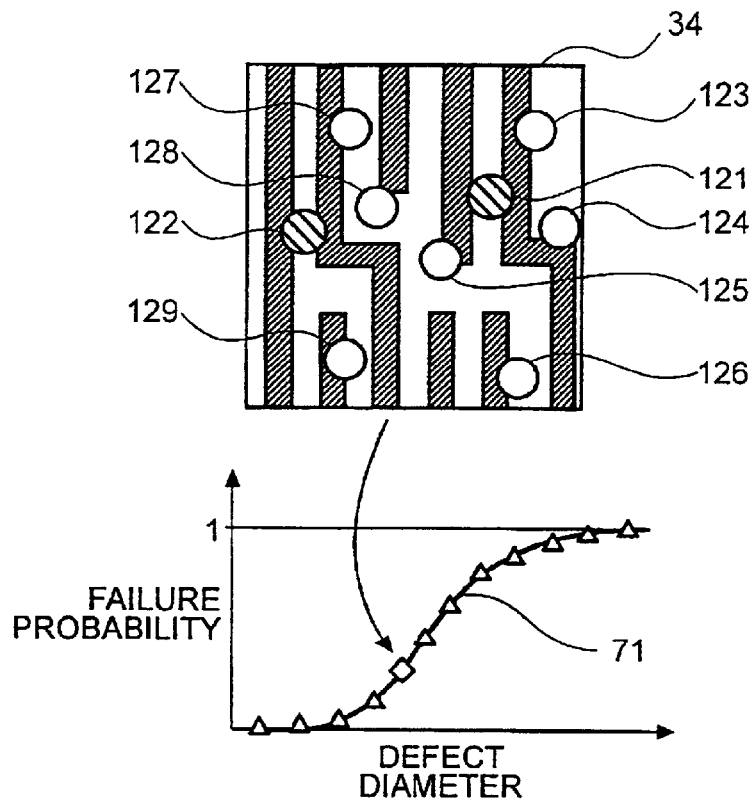
FIG. 7 is an example of a method for calculation of failure probability data.
Figure 8:
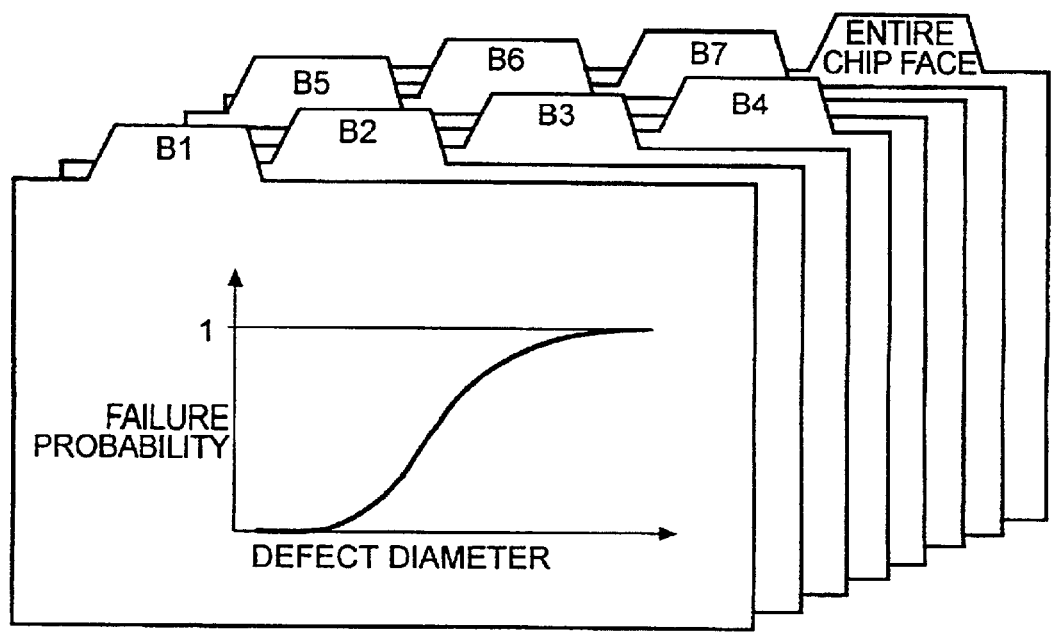
FIG. 8 is an example of an ensemble of failure probability data.

Referring now to FIGS. 6, 7, and 8, an explanation is given of one example of the method for calculating failure probability using the circuit layout data in accordance with a defect diameter.

FIG. 6 is an example of the circuit layout data. The circuit layout data are 2D graphics data of mask patterns for use during transfer of a circuit pattern of an LSI circuit by a photolithographic apparatus. Reference number 32 denotes a schematic diagram of a circuit layout, wherein rectangular frames B1 to B7 are the positions of LSI blocks 1 to 7, respectively. An enlarged view 33 of a portion of B6 indicated by oblique lines is shown. The white portions within the enlarged view 33 are patternless circuit portions whereas the gray portions constitute circuit pattern portions.

FIG. 7 is a diagram showing a method for calculating failure probability (kill ratio) data from the circuit layout data. This method is presently applied to yield prediction schemes as disclosed in Published Unexamined Japanese Patent Application Nos. 48-40376 and 8-162510 and also in C. H. Stapper, "Modeling of Defects in Integrated Circuit Photolithographic Patterns," *IBM Journal of Research and Development*, Vol. 28, No. 4, 1984. More specifically, the so-called Monte Carlo simulation is applied to the circuit pattern of each layer of the circuit layout data, thereby causing virtual circular defects of the same diameter to generate at random positions. Reference number 34 indicates an enlarged view of LSI block position B6 with the circuit patterns being collated with such virtual defects. In this example, virtual defects with oblique lines added to the circular frames of 121, 122 are electrical short circuit failures; in contrast, virtual defects indicated by the white circles 123–129 will not result in any electrical failures.

The failure probability in this example is two-ninths, wherein defects plotted along the vertical axis have failure probability and those plotted along the transverse axis are defect diameters shown as white rhombic plot points. Such simulation is performed for various virtual defects with different diameter values, and plotted as white triangles. A curve passing though the triangular plot points and rhombic plots is a failure probability data curve 71.

FIG. 8 is a pictorial representation of an ensemble or "assembly" of failure probability data items. Here, the simulation shown in FIG. 7 is performed with respect to each product type and each layer on a per-LSI-block basis, on a per-entire-ship-surface basis or on a per-2D-region basis, thereby to calculate the respective failure probability data. And, based on this, the information in layout data file 72 shown in FIG. 9 is obtained for the units of the respective LSI blocks.

Auxiliary storage device 63 also stores therein review conditions used for the selection of defects to be reviewed as will be described later, and programs for the selection of multiple defects to be reviewed, which also will be described later.

Figure 1:
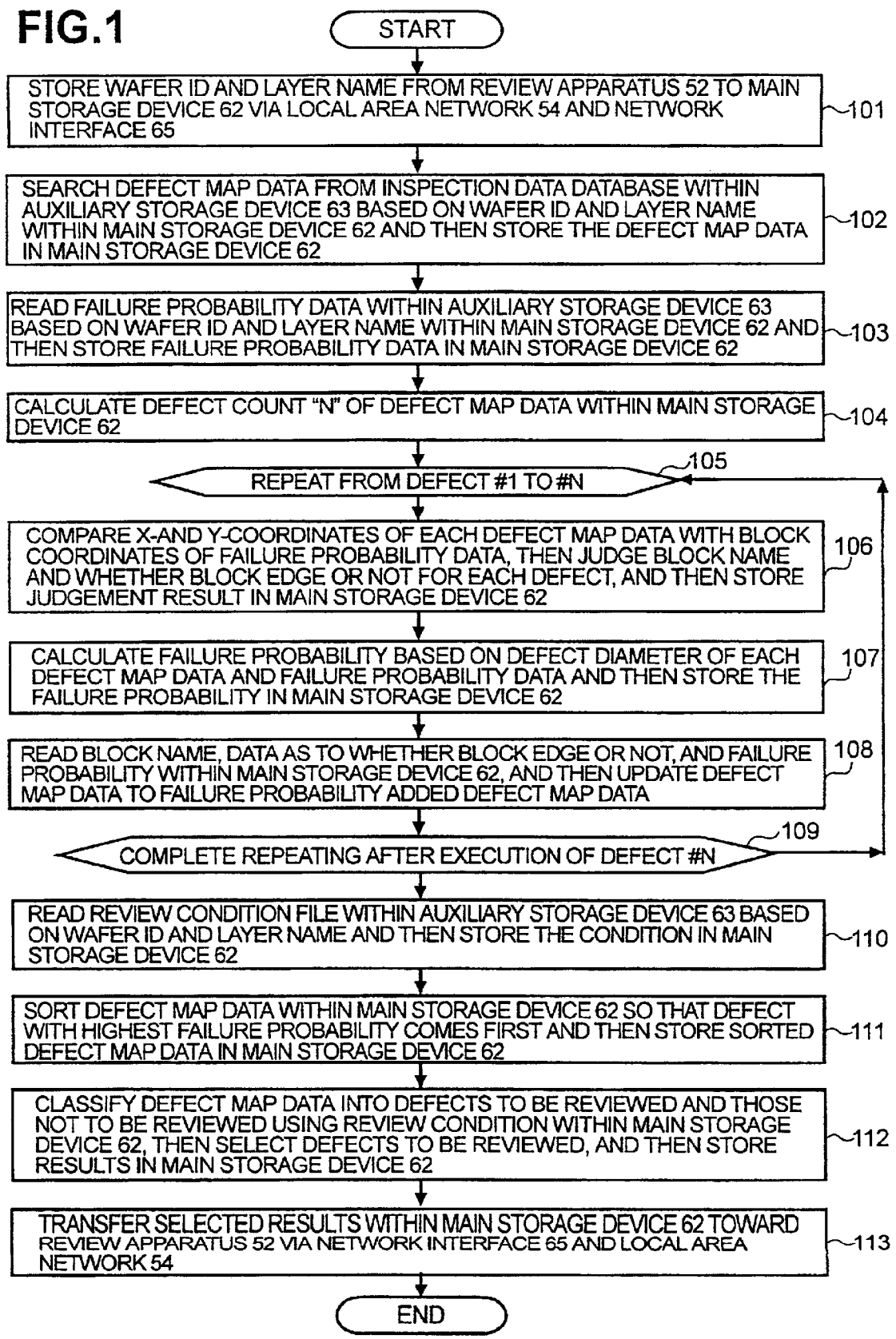
FIG. 1 is a diagram showing an example of the processing procedure applied to the selection of a defect or defects for review.

The flow of a series of processing tasks for selecting multiple defects for review will now be described with reference to FIG. 1.

A wafer that has passed the inspection by inspection apparatus 51 is set at review apparatus 52, which reads the wafer ID (step 101). In addition, the wafer's layer name is set up.

Upon input of the wafer ID and layer name, these information items are sent to main storage device 62 of analysis unit 60 through local area network 54 and network interface 65. Note that the wafer ID is the information indicative of a product type name, a lot number and a wafer number.

Step 102 searches any corresponding defect map data (see FIG. 3) to be stored in the auxiliary storage device 63 based on the received information of wafer ID and layer name, and then stores such searched defect map data into the main storage device 62.

Step 103 reads an ensemble of layout data 72 (see FIG. 9) within auxiliary storage device 63 based on the wafer ID and layer name being stored in main storage device 62, and stores it in the main storage device.

Next, step 104 calculates the number of defects from the defect map data stored in main storage device 62 at step 102, and thereafter step 105 executes the following processing, for each of defect numbers 1 to "N".

For each defect of the defect map data, step 106 compares the X- and Y-coordinates to the layout data block coordinates to determine or "judge" a block name to which the defect belongs while at the same time judging whether or not such defect's position is at a block edge, and then stores the result in main storage device 62. Here, determining whether the defect is in a block edge or not may be ascertained in such a way that if a distance from the defect to an LSI block edge is less than a predesignated threshold value, the defect is determined to be present at the block edge. An alternative approach is to represent the distance by coordinates indicative of an allowable range and then make a decision by determining whether the defect falls within the coordinate range. Because the defect's position coordinates are set by chip coordinates rather than wafer coordinates in this embodiment, it is possible to readily perform a comparison with all the above-noted layout data block coordinates for all the chips concerned. In case more than one type of LSI is formed in a single wafer, the comparison may be done while setting the layout data for each LSI.

Step 107 calculates a failure probability to be defined in its corresponding ensemble layout data 72 based on the defect map data's defect diameters stored in main storage device 62, then, stores the calculation result in main storage device 62.

Next, step 108 reads the block name, the data indicating whether or not the defect is at the block edge, and the failure probabilities which have been calculated at steps 106–108 and stored in main storage device 62, then generates failure-probability-added defect map data. FIG. 11 is an example of such failure-probability-added defect map data. The failure-probability-added defect map data 23 is such that the results obtained from the defect-containing block, whether it is an LSI block or not, and the failure probability are added to the defect map data 21 shown in FIG. 3. Step 109 repeats steps 106–108 with respect to all available defects.

Next, step 110 reads a conditions of review file within auxiliary storage device 63 based on the wafer ID and layer name stored in main storage device 62 and then stores it in the main storage device 62 (step 110). Here, the review condition is the one that may be freely set by users; for example, a specification for extraction of only those defects having a failure probability greater than or equal to a prespecified value; a specification for extraction of those defects that are not present at block edges; a specification for extraction of only those defects with defect sizes greater than or equal to a preselected value or, alternatively, less than or equal thereto; a specification for extraction of only those defects present in specified blocks, or a specification for extraction of a predetermined number of defects from each block. Alternatively, a user may employ a specification that combines some or all of these. An advantage of these schemes is that those defects which can cause electrical failures may be efficiently selected from among a large number of defects detected by the inspection apparatus. A practical and meaningful review condition is to select specific defects that influence production yield while excluding defects with no influence upon the yield.

FIG. 16 is an example of a conditions of review file. Reference number 41 indicates an example of a file that is stored in auxiliary storage device 63 and that permits a person in charge of defect analysis to establish an appropriate review specification from user interface 64 of analysis unit 60. In this example, review of a product type named LOGIC234 and layer named METAL1 is capable of letting a maximum of twenty defects be reviewed and, simultaneously, an instruction is given to review defects excluding those in block B5 and those present at the block edges of LSI blocks B1, B2, except for certain defects which have a failure probability greater than or equal to 0.30. Thus specific defects, out of all those detected by inspection apparatus 51, which satisfy these conditions will be reviewed by review apparatus 52.

Next, step 111 sorts the failure-probability-added defect map data 23 within main storage device 62 in serial order so that data with higher failure probabilities come before the others, and then stores the data in main storage device 62. FIG. 12 is defect map data 24 that has been sorted based on failure probability. The failure-probability-added defect map data 23 of FIG. 11 is recorded so that defects are listed in the order of highest failure probability to lesser failure probability. Note here that if review is done without regard to the failure probability then, obviously, this step and the step of calculating the failure probability (and any associated arrangements thereof) will no longer be required. However, in view of the fact that the failure probability is also a parameter or "barometer" that clearly indicates critical defects, it can be said that reviewing defects having higher failure probabilities is an effective way to review the most serious defects.

Next, step 112 classifies defect map data into the defects of interest and the defects of no interest according to the conditions of review in main storage device 62, then selects one or more defects to be reviewed, and stores the data in main storage device 62.

FIG. 13 is an example of a defect to be reviewed as selected from defect map data 23. Reference number 26 indicates an example with the top five defects selected from defect map data 23 and sorted according to the failure probability while excluding those defects found to be present at LSI block edges. An advantage is that any defects detected from the LSI block edges, which have a high likelihood of being noncritical, can be successfully excluded.

FIG. 14 is another example of the selection of defects to be reviewed using defect map data 24. Reference number 27 indicates an example with the top five defects being, specified for review, wherein the five defects have been selected from defect map data 24 and sorted based on failure probability while excluding those defects belonging to an LSI block b5. An advantage of this process is that any defects generated at b5, which are known in advance, based on experience, to be noncritical, are capable of being successfully excluded.

FIG. 15 is still another example of selection of defects to be considered for review using defect map data 23. Reference number 25 indicates a list of the top five defects from defect map data 24 sorted according to descending failure probability. Exactly how many high-priority defects are specified as the defects for review is determined from the actual processing rate of the review apparatus and/or LSI wafer production volume, or the like. Moreover, since the failure probability being calculated changes in value in accordance with the layout, i.e., the degree of density and coarseness of each block, it becomes possible for those defects with a tendency to become critical defects to be reviewed in accordance with the layout.

Finally, step 113 transfers the defects to be reviewed selection result from main storage device 62 to review apparatus 52 via network interface 65 and local area network 54. The review apparatus 52 reviews the defects in a highest priority order based on the defect selection result thus received. At this time, the coordinates of such defects have already been defined in the defect selection result; thus, it is possible to drive the review apparatus based on this information. Also note that if defects to be reviewed are selected because of the defect selection result, then a technique can be used whereby the order of review of the defects can be revised in order to review them efficiently. This technique may be executed by either review apparatus 52 or analysis unit 60.

Figure 17:
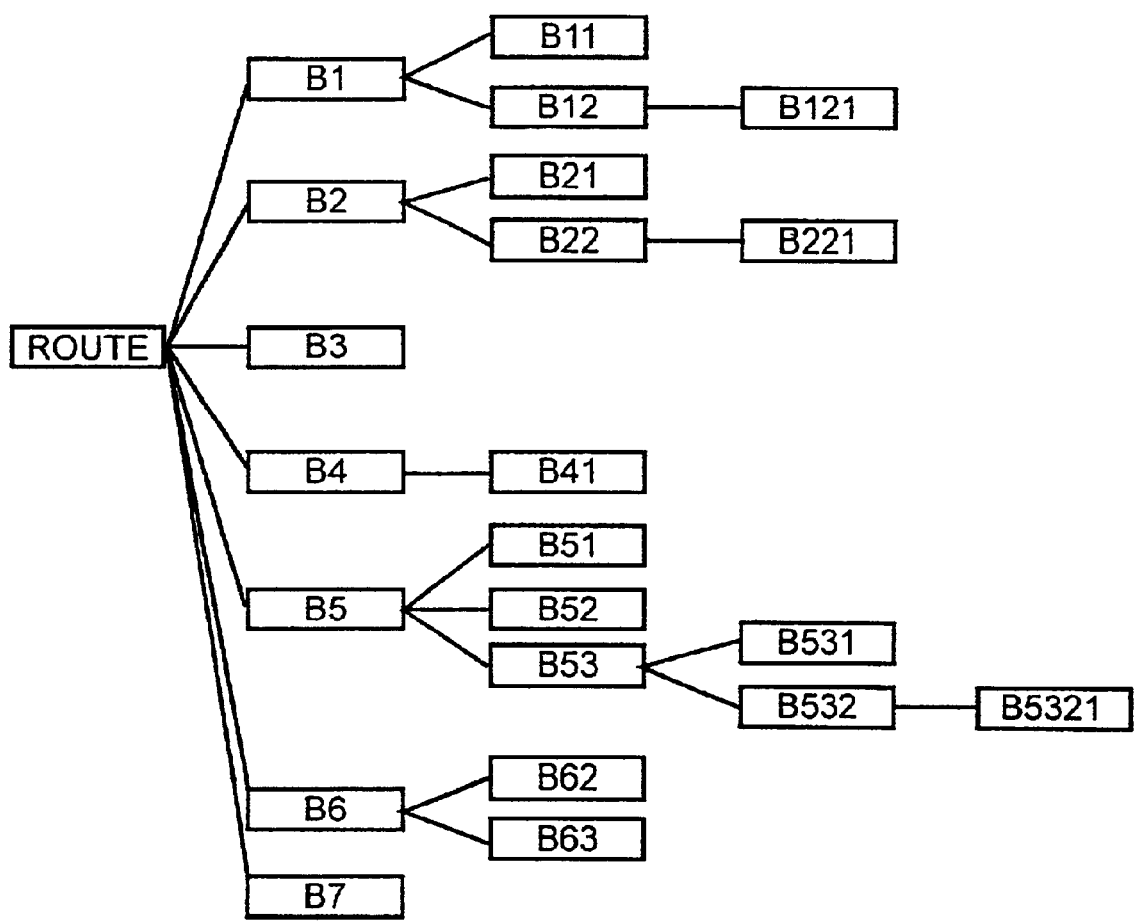
FIG. 17 is an exemplary block diagram of a circuit layout.

FIG. 17 shows one example of the structure of circuit layout data. Circuit layout data of a single LSI is generally designed to have a hierarchical structure in units of LSI blocks as shown in this figure. A "root" is to be understood to mean an entire LSI, wherein B1–B7 are LSI blocks. Furthermore, B11, B12, B21, B22, B41, B51, B52, B53, B61, B62, B121, B221, B531, B532 and B5321 are sub-blocks of the LSI blocks or, alternatively, further subblocks of subblocks. In this example, LSI blocks B1–B7 are included in the root. In addition, subblocks B11 and B12 are involved in LSI block B1. Further, B121 is included as a subblock of B12. Here, the LSI block's hierarchical structure is hierarchical in functionality and, thus, does not mean any layer of the LSI. Several layers are present in the same block and subblock. Additionally the same layer's circuit pattern is included in different blocks. Because of this, the simulation for obtaining the failure probability that was explained in conjunction with FIG. 7 is carried out such that a circuit pattern of the same layer is extracted from each block of this structure to thereby prepare per-layer data.

Figure 18:
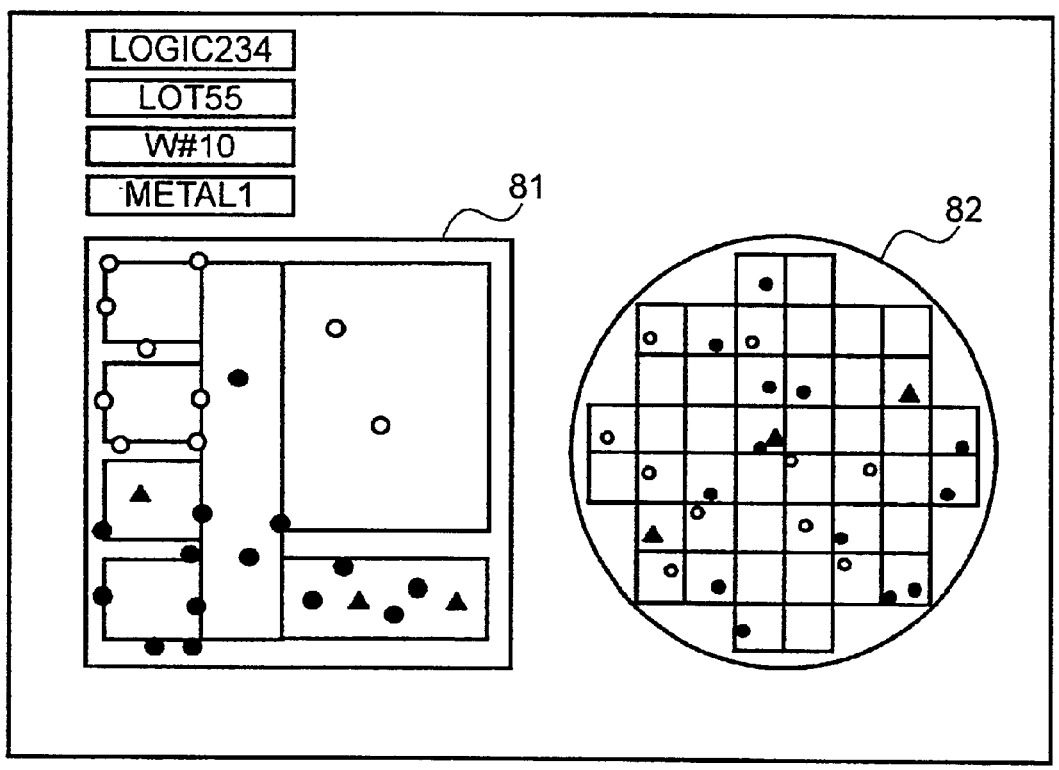
FIG. 18 is an exemplary on-screen display of an inspection system.

FIG. 18 is an example of an on-screen display of analysis unit 60. This drawing shows defect map data of a layer named METAL1 with a product type name LOGIC234, a lot number LOT55 and a wafer number 10. This result is obtained after having selected the defects to be reviewed while using the review conditions 41 shown in FIG. 16. Image displays a defect position distribution with such defect map data plotted by dots, using the coordinates within a chip, and provides a display superimposed on a schematic diagram of the circuit layout. Image 82 displays defect map data at wafer level. Both images display the same defect map data. Black triangles are the selection results of defects to be reviewed. Here, three defects satisfied review conditions 41. White circles are defects as determined under review conditions 41 to be excluded from the defects to be reviewed irrespective of the failure probability thereof; whereas black circles are defects that were never candidates for review because their failure probabilities were less than 0.30. In this way, simultaneously displaying the defects as selected for review along with on-chip defect distribution and/or circuit layout, as well as showing the wafer level, makes it possible to recognize defects for review with increased understanding. Here, when displaying a schematic diagram of a circuit layout such as image 81, the detailed circuit layout as presented in FIG. 17 is no longer required. In order to rapidly display the entirety of a chip with the circuit layout data, it is effective to compress the circuit layout data in auxiliary storage device 63 as bitmap data.

Figure 19:
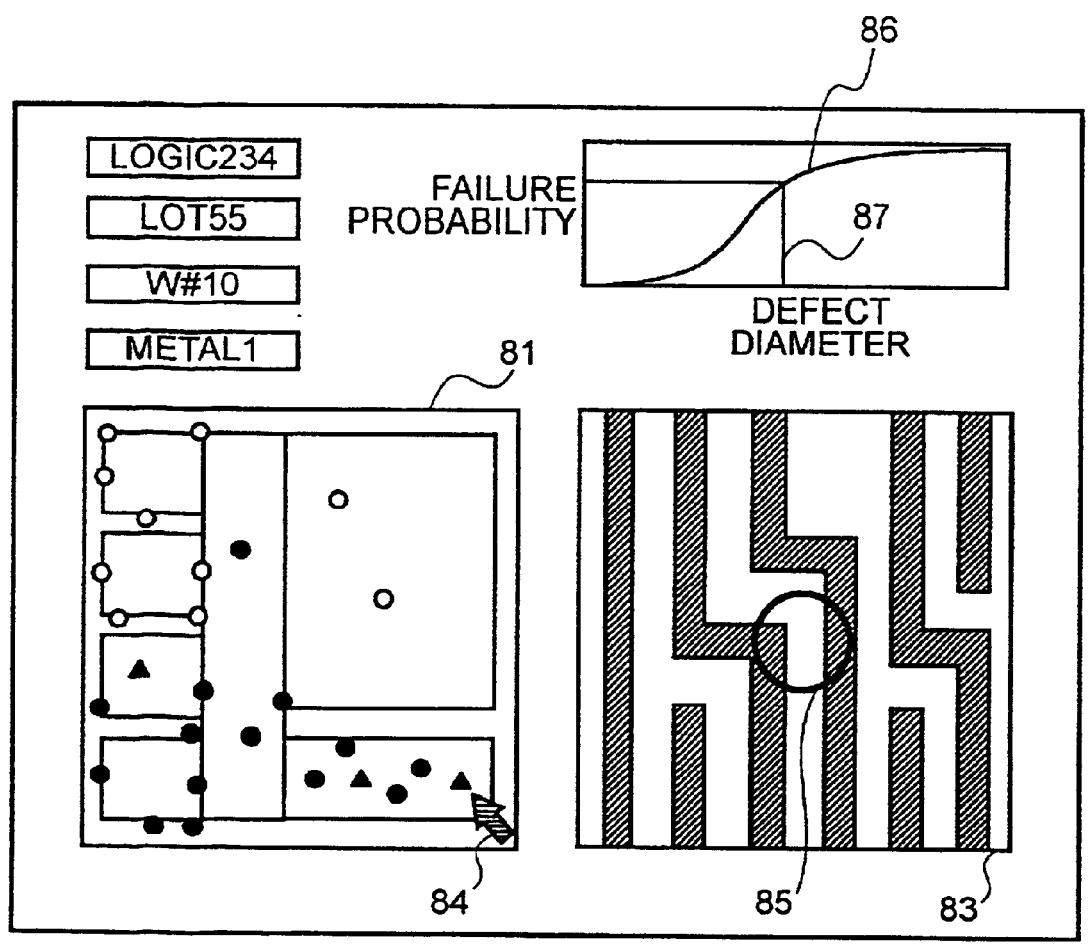
FIG. 19 is another exemplary on-screen display of the inspection system.

FIG. 19 is another example of the on-screen display of analysis unit 60. This drawing shows the same defect map data as in FIG. 18. Image 81 is the same as that of FIG. 18. Image 83 is a result obtained through a process having the step of clicking while pointing a cursor 84 at a single defect within image 81 to search for and display the layout data of circuitry near or around the defect. In image 83, a circular frame 85 is drawn with the position of the defect at the center, pursuant to the size of the defect, thereby enabling easy recognition of the relation of this defect to the circuit pattern prior to executing the review. In addition, image 86 is a graph depicting a failure probability data curve of an LSI block in which the defect clicked with cursor 84 is present, image 87 is the size of that defect. Visually displaying both the defect size and the failure probability data at the same time, makes it possible to confirm the reason for selecting this defect for review. In this example, the review conditions are to be determined by selection of a review of unnecessary circuit blocks, or of block edges or by using an alternative definition of failure probability, based on results obtained after executing a review without any inspections and conditions.

So far, the same layout data file (FIG. 9) has been used without regard to the on-wafer chip positions; however, in many cases, the rate of occurrence of critical defects can differ within wafer surfaces. In particular, the quest for larger wafer diameters makes such a phenomenon more appreciable. To cope with this phenomenon, one approach is to perform defect selection by employing in combination prior known random sampling techniques and the above-discussed method for selecting defects by failure probability. In other words, both the process of reviewing defects through prior art random sampling and the above-stated process of reviewing by using the failure-probability-based defect selection methodology are performed at the same time. This also makes it possible to uniformly select on-wafer defects. Alternatively, similar effects are obtainable either by extracting them through random sampling of failure probability results greater than or equal to a pre-specified value or by performing random sampling of those defects not present at any block edges. Another alternative approach is to subdivide an entire wafer surface into specific areas by use of chip coordinates, with each of the areas thus divided then subject to defect extraction. In this case, it would readily occur to those skilled in the art that the finer the areas, the more uniform the review of the entire wafer face.

It has been stated that a more efficient inspection of semiconductor chips than provided by the prior art is achievable by using a specific method during inspection of particles and pattern defects of wafers forming electronic devices, which method includes the steps of sampling certain defects having a high potential for causing electrical failures, and then giving such defects with high-priority review. Similarly, it is also possible to review the defects having a high potential, in themselves, for becoming electrical failures.

In accordance with the present invention, the use of layout information makes it possible to improve inspection efficiency by determining defects for high-priority review, thereby improving the resulting yield of production.

What is claimed is:

1. An inspection system comprising:
   an inspection apparatus for detecting positions and sizes of particles or pattern defects on an object to be inspected;
   an image taking apparatus for taking images of said particles or said pattern defects as detected by said inspection apparatus; and
   an analysis unit operatively coupled to said inspection apparatus and said image taking apparatus, said analysis unit including:
      a storage device for storing therein inspection data produced by said inspection apparatus and position information of regions of a circuit pattern to be formed on said object;
      a calculation device for identifying particles or pattern defects that are correspondingly positioned in said regions, and calculating failure probabilities for said particles or said pattern defects positioned in said regions based on their sizes, said failure probabilities further being based on location of said particles or said pattern defects in said regions; and
      a selection device for selecting particles or pattern defects whose calculated failure probabilities are greater than or equal to a predetermined threshold.

2. The inspection system according to claim 1, wherein said regions are circuit blocks as formed within an LSI chip.

3. The inspection system according to claim 2, wherein said position information of said circuit blocks is generated from mask layout data forming an LSI chip.

4. The inspection system according to claim 1, further comprising a simulation device for generating virtual defects at random positions with respect to circuit graphics obtainable from mask layout data forming said circuit pattern, and computing said failure probabilities from connection relationships of said circuit graphics and said defects.

5. The inspection system according to claim 1, wherein said position information of said regions is generated from mask layout data forming an LSI chip.

6. A method for manufacturing semiconductor devices comprising the steps of:
   a fabrication step for forming circuit patterns on or over a wafer, said circuit patterns constituting a plurality of semiconductor chips;
   an inspection step for detecting positions and sizes of particles or pattern defects of said wafer;
   identifying positions and sizes of those of said particles or said pattern defects located in a region of said circuit patterns that constitute one of said semiconductor chips;
   a calculation step for calculating failure probabilities based on sizes of said particles or said pattern defects in said region and on their location in said region;
   an extraction step for extracting positions of said particles or said pattern defects with calculated failure probabilities greater than or equal to a predefined threshold; and
   producing images of said particles or said pattern defects extracted at said extraction step.

7. A method for manufacturing semiconductor devices according to claim 6, wherein said regions are circuit blocks within an LSI chip.

8. A method for manufacturing semiconductor devices according to claim 7, wherein said LSI chip is a system LSI and said circuit blocks include memory portions and logic portions.

* * * * *